United States Patent [19]

Fifolt

[11] Patent Number: 4,499,024

[45] Date of Patent: Feb. 12, 1985

[54] CONTINUOUS PROCESS FOR PREPARING BISFLUOROXYDIFLUOROMETHANE

[75] Inventor: Michael J. Fifolt, Grand Island, N.Y.

[73] Assignee: Occidental Chemical Corporation, Niagara Falls, N.Y.

[21] Appl. No.: 545,021

[22] Filed: Oct. 24, 1983

[51] Int. Cl.³ ............................................. C07C 71/00
[52] U.S. Cl. ................................................. 260/453 R
[58] Field of Search .................... 260/453 R; 568/604; 570/134, 150

[56] References Cited

U.S. PATENT DOCUMENTS 3,394,163  7/1968  Kroon ............................. 260/453 R

OTHER PUBLICATIONS

Hohorst, et al.; C.A. 69 (1968), 51462j.
Hohorst, et al.; J.A.C.S., 89, (1967), pp. 1809–1810.
Thompson; J.A.C.S., 89, (1967), pp. 1811–1813.
Cauble, et al.; J.A.C.S., 89, (1967), p. 1962.

*Primary Examiner*—Joseph P. Brust
*Attorney, Agent, or Firm*—James F. Tao; William G. Gosz

[57] ABSTRACT

Bisfluoroxydifluoromethane is prepared by the continuous reaction of carbon dioxide and fluorine in the presence of a cesium fluoride catalyst. The reaction is preferably conducted at a temperature in the range of from about $-50°$ C. to about $200°$ C. and a mole ratio of $CO_2:F_2$ in the range of from about 0.2 to about 0.95.

1 Claim, No Drawings

CONTINUOUS PROCESS FOR PREPARING BISFLUOROXYDIFLUOROMETHANE

BACKGROUND OF THE INVENTION

The present invention relates to a continuous process for preparing bisfluoroxydifluoromethane, hereinafter designated as "BDM", which comprises reacting carbon dioxide with fluorine in the presence of a cesium fluoride catalyst.

Bisfluoroxydifluoromethane is a useful reagent for chemical synthesis reactions such as direct aromatic fluorination reactions. In such aromatic substitution reactions, the reaction of BDM with a suitable aromatic substrate results in the addition of a fluorine atom to the aromatic nucleus. This may result in the formation of unique fluorinated aromatic compounds which cannot be readily prepared using more conventional fluorinating agents. As illustrated by the foregoing, BDM is a useful reagent which has potential commercial applications in many organic synthesis reactions.

Bisfluoroxydifluoromethane has been previously prepared using a variety of methods. One method involves the fluorination of sodium trifluoroacetate and has the disadvantage of low yields and expensive reactants. Another method reacts fluorine with an alkali metal oxalate, such as sodium oxalate, in the presence of an alkali metal or alkaline earth metal fluoride. See the disclosure in U.S. Pat. No. 3,394,163. This method requires low temperature conditions for both the reaction and separation of BDM from reactants. In addition, this reaction also suffers from low product yields, and alkali metal oxalates are comparatively expensive for commercial processes. See, for example, P. G. Thompson, *Journal of the American Chemical Society*, Vol. 89, pages 1811 and 1813 (1967), which also describes the fluorination of sodium oxalate using the static bed process. Product yields of only 1% to 15% of BDM were achieved using this process.

A number of other processes are reported in the literature for preparing BDM. An article by F. A. Hohorst and J. M. Shreeve appearing in *Inorganic Synthesis*, Vol. 11, pages 143–147 (1968), describes the preparation of BDM by the static fluorination of carbon dioxide in the presence of anhydrous cesium fluoride at −78° C. Low temperature reaction conditions are required to preclude the formation of $CF_3OF$ and $OF_2$. The reaction requires approximately six hours and is carried out in an autoclave under essentially static conditions. In addition, a substantial excess of fluorine is required, e.g. nine moles of fluorine per mole of carbon dioxide. A related article by F. A. Hohorst and J. M. Shreeve appears in the *Journal of the American Chemical Society*, Vol. 89, pages 1809–10 (1967).

It is therefore a primary objective of the present invention to provide a continuous process for producing BDM in high yield using relatively mild reaction conditions.

SUMMARY OF THE INVENTION

The present invention is directed to a continuous process for preparing bisfluoroxydifluoromethane comprising the reaction of carbon dioxide with fluorine in the presence of a cesium fluoride catalyst. Preferably, the reaction is conducted at a temperature in the range of from about −50° C. to about 200° C. and a $CO_2:F_2$ mole ratio in the range of from about 0.20 to about 0.95.

DESCRIPTION OF THE PREFERRED EMBODIMENTS

According to the present invention, a process for preparing bisfluoroxydifluoromethane comprises the continuous reaction of carbon dioxide with fluorine in the presence of a catalytic amount of cesium fluoride.

The starting materials of the present invention (carbon dioxide and fluorine) are easily obtainable and comparatively inexpensive. The mole ratio of reactants ($CO_2:F_2$) is preferably maintained in the range of from about 0.20 to about 0.95, and most preferably from about 0.40 to about 0.70. Higher levels of $CO_2$ generally produce undesirable amounts of unreacted materials, while higher levels of fluorine do not result in improvements in efficiency or yield.

The reactants can be introduced as a mixed gas stream into a continuous reactor, such as a nickel or nickel-lined tube, which contains particles or powder of cesium fluoride. The cesium fluoride is preferably in a high surface area physical form. The reaction can be conducted at a temperature in the range of from about −50° C. up to about 200° C., but a preferred temperature range is from about 20° C. to about 30° C.

Under the reaction conditions of the present invention, both reactants and products are present as gases. The principal impurities present in the product stream are $CF_3OF$, $CO_2$ and $CF_4$, although trace amounts of fluorinated compounds such as $CF_3OOCF_3$ can also be present. $CO_2$ and $CF_4$ are generally inert and do not adversely affect the reactivity of BDM with other compounds. Therefore, these compounds generally will not have to be separated from the product stream. However, if a high degree of product purity is essential, separation can be easily accomplished by liquefaction. $CF_3OF$ is a reactive species which is also not detrimental to produce purity since it generally has the same basic reactivity as BDM.

The following examples are intended to further illustrate the various embodiments and advantages of the present invention without limiting it thereby.

EXAMPLE 1

Fluorine and carbon dioxide were flowed through a nickel tube containing 330 grams of cesium fluoride. The nickel tube was heated to 150° C. with the fluorine and carbon dioxide in a 4:1 mole ratio, respectively. The effluent from the reaction was trapped in a metal trap cooled with dry ice and ethanol. The trapped material was then distilled into another cylinder for storage. $F^{19}NMR$ of a solution of fluorotrichloromethane that had been saturated at −78° C. with the isolated gas from the reaction disclosed that a mixture of fluoroxytrifluoromethane and bisfluoroxydifluoromethane was present.

EXAMPLES 2–20

The procedure of Example 1 was repeated using a variety of reaction conditions. The cesium fluoride catalyst employed had a surface area of 0.83 m²/gram. Flow rates are measured in standard cubic centimeters per minute (SCCM).

In Examples 2–10, Argon was used as a diluent for fluorine, while Helium was used for this purpose in Examples 11–20. This was done to simplify the analysis of the product by Gas Chromatography.

TABLE I

| Example No. | Flow SCCM CO$_2$ | Flow SCCM F$_2$ | Mole Ratio CO$_2$:F$_2$ | Temp °C. Reactor | CF$_2$(OF)$_2$ | CF$_3$OF | CO$_2$ | CF$_4$ |
|---|---|---|---|---|---|---|---|---|
| 2  | 30 | 60 | .48 | 24 | 90 | 1 | 5  | 2  |
| 3  | 35 | 60 | .55 | 26 | 91 | — | 7  | 1  |
| 4  | 25 | 60 | .40 | 24 | 91 |   | 6  | 1  |
| 5  | 25 | 50 | .44 | 24 | 92 | 1 | 3  | 3  |
| 6  | 30 | 60 | .48 | 25 | 90 | 1 | 4  | 4  |
| 7  | 35 | 60 | .55 | 24 | 92 | 1 | 5  | 2  |
| 8  | 25 | 60 | .40 | 24 | 90 | 1 | 3  | 3  |
| 9  | 30 | 60 | .48 | 25 | 92 | 1 | 2  | 4  |
| 10 | 30 | 60 | .48 | 25 | 99 | — | —  | —  |
| 11 | 30 | 60 | .48 | 25 | 92 | — | 2  | 4  |
| 12 | 30 | 60 | .48 | 25 | 96 | — | 1  | 2  |
| 13 | 25 | 60 | .40 | 25 | 86 | — | 2  | 10 |
| 14 | 30 | 60 | .48 | 27 | 95 | — | 1  | 4  |
| 15 | 35 | 60 | .55 | 27 | 95 |   | 4  | 1  |
| 16 | 40 | 60 | .63 | 28 | 88 |   | 11 |    |
| 17 | 45 | 60 | .72 | 29 | 80 |   | 18 |    |
| 18 | 50 | 60 | .79 | 29 | 76 |   | 23 |    |
| 19 | 60 | 60 | .95 | 29 | 66 |   | 32 |    |
| 20 | 30 | 60 | .48 | 25 | 93 | — | —  | 6  |

While various embodiments and exemplifications of this invention have been shown and described in the specification, modifications and variations thereof will be readily appreciated by those skilled in the art. It is to be understood, therefore, that the appended claims are intended to cover all such modifications and variations which are considered to be within the scope and spirit of the present invention.

What is claimed is:

1. A continuous process for preparing bisfluoroxydifluoromethane comprising the steps of:

(a) introducing a mixed gas stream containing carbon dioxide and fluorine into a continuous reactor at a temperature of from about 20° C. to about 30° C. and in a mole ratio of carbon dioxide to fluorine of about 0.40 to about 0.70, said reactor containing a catalytic amount of cesium fluoride, (b) maintaining the temperature of the reactor in the range of from about 20° C. to about 30° C., (c) collecting the exit gases from the reactor, and (d) recovering bisfluoroxydifluoromethane from the exit gases.

* * * * *